(12) United States Patent
Almodovar

(10) Patent No.: US 9,192,376 B2
(45) Date of Patent: Nov. 24, 2015

(54) ROTATIONAL DRIVER

(76) Inventor: Luis Jose Almodovar, San Juan, PR (US)

( * ) Notice: Subject to any disclaimer, the term of this patent is extended or adjusted under 35 U.S.C. 154(b) by 642 days.

(21) Appl. No.: 12/554,795

(22) Filed: Sep. 4, 2009

(65) Prior Publication Data

US 2009/0326559 A1    Dec. 31, 2009

Related U.S. Application Data

(63) Continuation-in-part of application No. 11/969,660, filed on Jan. 4, 2008, now abandoned.

(51) Int. Cl.
*A61B 17/062* (2006.01)
*A61B 17/04* (2006.01)
*A61B 17/00* (2006.01)
*A61B 17/29* (2006.01)
*A61B 19/00* (2006.01)

(52) U.S. Cl.
CPC ........... *A61B 17/062* (2013.01); *A61B 17/0491* (2013.01); *A61B 2017/0042* (2013.01); *A61B 2017/2929* (2013.01); *A61B 2017/2946* (2013.01); *A61B 2019/467* (2013.01)

(58) Field of Classification Search
CPC ........... A61B 17/0469; A61B 17/0482; A61B 17/062; A61B 17/0491; A61B 17/06061; A61B 2017/2929
USPC .......................... 606/139, 144–148, 205–209
See application file for complete search history.

(56) References Cited

U.S. PATENT DOCUMENTS

| | | | | |
|---|---|---|---|---|
| 2,601,564 | A * | 6/1952 | Smith | 606/144 |
| 5,501,690 | A * | 3/1996 | Measamer et al. | 606/146 |
| 5,582,617 | A * | 12/1996 | Klieman et al. | 606/170 |
| 5,897,563 | A * | 4/1999 | Yoon et al. | 606/144 |
| 5,954,731 | A * | 9/1999 | Yoon | 606/144 |

* cited by examiner

*Primary Examiner* — Kathleen Holwerda
(74) *Attorney, Agent, or Firm* — Eugenio J. Torres-Oyola; Ferraiuoli LLC

(57) ABSTRACT

A rotational driver that comprises a interactive portion, wherein each interactive portion comprises a first extended member and a second extended member, a rotational system and a linear motion system, wherein the rotational driver permits a left or right handed surgeons to perform the surgical suturing procedure in a less complicated and more secure way by allowing more control over the suturing needle and the area to be stitched, even when the suturing area is small, deep, and/or restricted.

13 Claims, 14 Drawing Sheets

ROTATIONAL DRIVER

RELATED APPLICATIONS

This application is a continuation in part related to U.S. patent application Ser. No. 11/969,660 filed on Jan. 4, 2008 now abandoned.

BACKGROUND OF INVENTION

1. Field of the Invention

The present invention relates generally to a surgical suturing device, more specifically, to a ergonomic Rotational Action Needle Driver which enhance the tissue suturing procedure, particularly the one performed on restricted, deep and less accessible locations, by incorporating a pull-locking mechanism that prevents problems associated with loss of needle control during the suturing procedure and the ones associated with prior needle driver's handedness. It also enhances the control surgeons has over the suturing needle by enabling a rotational movement while driving the suturing needle through the tissue that permits to place the needle in the right location in order to continue the subsequent steps of the suturing cycle.

2. Background of the Invention

Surgical procedures have proliferated among the medical practice as new treatments are developed to effectively treat common and extraordinary conditions. The spectrum of invasiveness goes from simple tissue suturing of small open wounds to complicated procedures as those performed in vascular or neurological surgeries. It is undoubted that each and every step on any surgical procedure is of great importance and could cause negative consequences for the patient if it is inadequately performed. The suturing procedure, in particular, could end in serious consequences for the patient if negligently conducted, causing damages to adjacent tissues or even organs.

It is known that the suturing procedure consumes a considerable amount of time of the surgical treatment. Simplification of the suturing procedure by developing more effective suturing devices will reduce the time spent on that task and at the same time will reduce the risk of negative consequences arising from damages caused to adjacent tissues or organs.

Generally, the instruments used in suturing procedures are the suturing material, the suturing needle and the suturing driver. Efforts made to reduce the suturing time and to enhance the suturing procedures' safety have been focused on performing needle driver's modifications. One of the generally unattended deficiencies of the available needle drivers is the handedness of its designs. For instance, Scalan, Jr, in U.S. Pat. No. 4,161,951 discloses a device to drive a needle through the bony structure of the sternum and to facilitate closing the chest cage after thoracic surgery.

Similarly, Yoon in U.S. Pat. No. 5,759,188 discloses a suturing instrument comprising a needle driver and a needle catcher to be used in laparoscopic procedures.

Alternatively, Stoianovici in U.S. Pat. No. 6,400,979 B1 discloses a method of performing a radiological imaged guided percutaneous surgery with a system including a radiological image generating device for generating images of the targeted area, and a needle insertion mechanism disposed adjacent the image generating device.

On the other hand, McGarry U.S. Pat. No. 6,520,973 B1 discloses vascular anastomosis incorporating sutures for joining a graft blood vessel to a target blood vessel such as the aorta or coronary artery. The entire content of all of the above cited U.S. patents are hereby incorporated by reference.

However, one of the generally unattended deficiencies of the available needle drivers is the handedness of its designs. Ordinarily, needle drivers are designed to fit right handed users. Thus, left handed users have difficulties performing the suturing procedure. The right handedness of those devices further affects the capacity of left handed surgeons to lock and unlock the drivers' locking mechanism. This increases the risks of negative outcomes for patients from wrong needle driver maneuverings. That is why latest suturing devices very often fail to ease the drivers handling. The available drivers without handedness are very delicates because are mostly designed for ocular and microvascular procedures.

SUMMARY OF THE INVENTION

The disclosed invention provides an effective suturing device that enhances the maneuvering and safety of suturing procedures. The rotational driver comprises a interactive portion, wherein each interactive portion comprises a first extended member and a second extended member, a rotational system a linear motion system, wherein said first extended member comprises a first distal end, a first proximal end and a first main extended member body, wherein said first main member body in between said first distal end and said first proximal end, wherein said first distal end comprises a first contact distal end, wherein said second extended member comprises a second distal end, a second proximal end and a second main member body, wherein said second main member body is between said second distal end and said second proximal end, wherein said second distal end comprises a second contact distal end, wherein said rotational system comprises a rotational actuator mechanically coupled to at least an action transmitter mechanism, wherein said action transmitter mechanism is mechanically connected to said first extended member providing rotating action upon said first distal end; and wherein said first distal end and said second distal end contact each other in an oblique manner by means of said linear motion system, wherein said linear motion system comprises mechanical means to provide displacement of said second distal end with respect to said first distal end and wherein said second distal end displacement exert compressing force at said first distal end, wherein said compressing force is concentrated at said first contact distal end and said second contact distal end by means of said oblique contacts.

As an example, the rotational driver is used in a suturing procedure consisting of a rotational suturing needle driver that comprises an ergonomical handle that eases the suturing process to right and left handed users. It also comprises a locking mechanism that permits users to maintain the needle tightly fixed to the needle driver in order to have a best control over the needle and the movements related to the suturing process. The disclosed embodiments also contain a rotational knob, as the rotational actuator, that provides additional control over the movements related to the suturing procedure. It permits the user to position the suturing needle at the exact angle at which the suturing material has to be inserted into the tissue.

As mentioned, the present invention overcomes the inability of the prior art to foresee the need of an ergonomical suturing needle driver that permits left and right handed users to performed safe suturing procedures. Furthermore, the invention is intended to provide an ergonomical suturing needle driver comprising a pull locking mechanism that can be effectively operated by left and right handed users.

Another deficiency presented by the prior art is the lack of disclosure of needle driver having a rotational mechanism that permits to fix the needle to a specific angle before inserting it into the tissue and combining the said rotation with ergonomic characteristics in order to facilitate the suturing processes.

None of the prior art considered above, taken either simply or in combination teaches the use of a suturing needle driver suitable to left and right handed users and comprising a pull locking mechanism and a rotational mechanism. In light of the foregoing, it will be appreciated that what is needed in the art is a suturing needle driver lacking of handedness and combining a pull locking mechanism and a rotational mechanism. Thus, the object of the present invention is to provide a surgical device that eases the suturing procedure associated with deep, restricted areas.

Another object of the present invention is to provide a surgical suturing needle driver that permits to grasp, secure and rotate a curved surgical needle without requiring a rotational motion at the surgeon's wrist.

It is the object of the present invention to provide a surgical suturing needle driver which incorporates a pull-locking rotational mechanism that secures the needle to the needle driver and permits to diminish the number of maneuvers actually needed for performing the surgical suturing process, reducing the risk of damaging peripheral tissues.

It is a further object of the present invention to provide an ergonomically designed suturing needle driver that eliminates the difficulties associated with needle driver maneuvering that arise from the handedness of that kind of instrument.

The system of the invention itself, both as to its configuration and its mode of operation will be best understood, and additional objects and advantages thereof will become apparent, by the following detailed description of a preferred embodiment taken in conjunction with the accompanying drawing.

When the word "invention" is used in this specification, the word "invention" includes "inventions", that is, the plural of "invention". By stating "invention", the Applicant does not in any way admit that the present application does not include more the one patentable and non-obviously distinct invention and Applicant maintains that the present application may include more than one patentably and non-obviously distinct invention. The Applicant hereby asserts, that the disclosure of the present application may include more than one invention, and, in the event that there is more than one invention, that these inventions may be patentable and non-obvious one with respect to the other.

Further, the purpose of the accompanying abstract is to enable the U.S. Patent and Trademark Office and the public generally, and especially the scientists, engineers, and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

DESCRIPTION OF THE PREFERRED EMBODIMENTS

Figure 1:
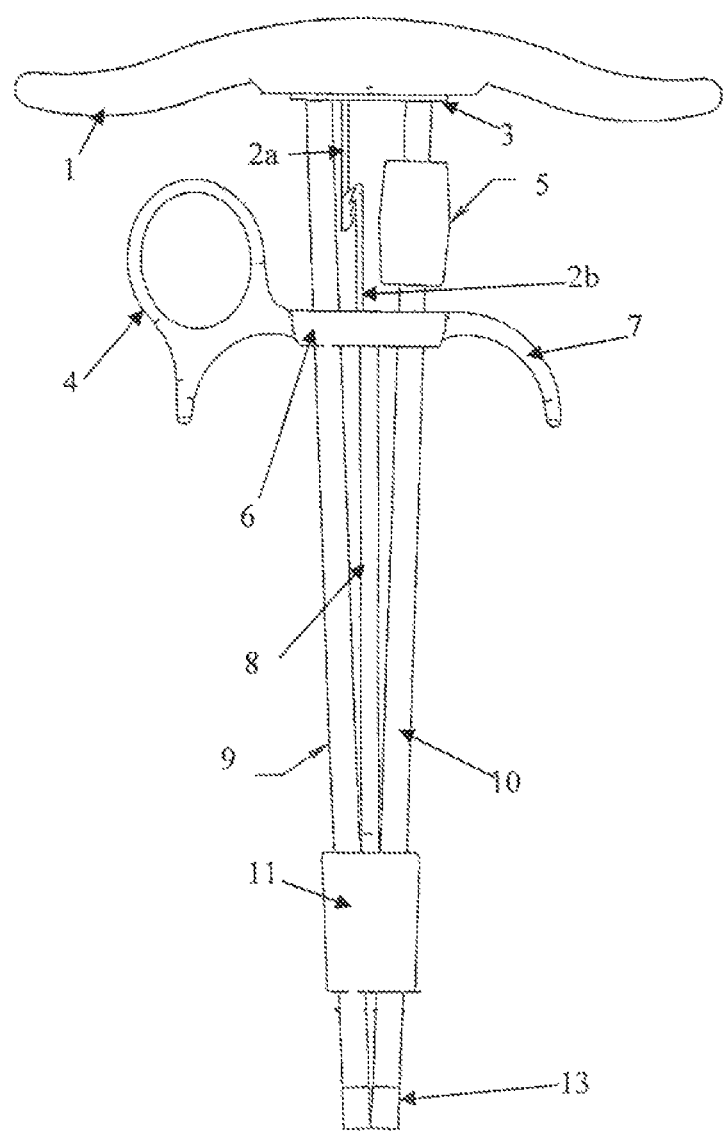
FIG. 1 shows a two-dimensional view of the Pull-locking Rotational Action Needle Driver device.

Turning to the diagram, FIG. 1 shows a first embodiment of the rotational driver comprising an interactive portion, wherein each interactive portion comprises a first extended member and a second extended member, such as two rods 9, 10 which approximate to each other resembling a pair of chop-sticks. Each extended member comprises a first distal end, a proximal end and a main extended member body, wherein said main member body in between said distal end and first proximal end, wherein said first distal end comprises a first contact distal end. At the distal end of each rod 9, 10 the surface is fluted creating a needle-grasping portion 13. The proximal ends of the rods 9, 10 have round contours. These rounded ends are embedded in its corresponding sockets located in the handle 1 of the invention. The handle 1 is ergonomically designed to rest against surgeon's palm his hand, permitting its proper use to right and left handed surgeons. The surgeon will maintain the handle 1 fixed to the palm his hand by using his thumb. The rods 9, 10 are fixed to the sockets by a transverse plate 3. The proximal ends serve as pivot points and rotational axis as the rods 9, 10 move towards or away from each other. The rods 9, 10 are surrounded near its distal ends by a harness 11 that comprises two independent channels, one for each rod 9, 10. The channels are slightly wider than the rods 9, 10. The harness 11 is connected to the pulling piece 6 by means of a connecting bar 8. The pulling piece 6 is designed as the harness 11 but is wider than the harness 11. The width difference is provoked by the angle created between the rods 9, 10 at its proximal ends. The pulling piece 6 comprises two pulling tabs 4, 7. Surgeon is supposed to place his middle finger around the inferior pulling tab 4. The index finger can be placed around the superior pulling tab 7 when further control is needed during suturing maneuvers. The ring and little fingers may rest against the handle 1. A locking mechanism 2a, 2b is located between the pulling piece 6 and the handle 1. It comprises two parallel small bars. One bar is attached to the pulling piece 6 and the other to the transverse plate 3. Each bar has triangular shaped teeth at its distal ends. The bar connected to the transverse plate 3 has three teeth and the one connected to the pulling piece 6 has one tooth. The bars are parallel positioned in order to make the teeth of one bar to meet against the other's tooth. The locking mechanism 2a, 2b is shifted to one rod 9, in order to make space for a turning knob 5 that is placed around the other rod 10. The turning knob 5 will be operated with the surgeon's thumb. The turning knob 5 permits to rotate the rods 9, 10 and, consequently, the needle.

When the suturing procedure begins, the curved needle is perpendicularly placed at the distal end 13 of the invention. For the needle to be tightly fixed to the invention, the surgeon has to pull the pulling piece 6 towards the handle 1. This makes the harness 11 to move toward the handle 1 too, making the rods 9, 10 to come closer and consequently tightening the needle. The movement towards the handle 1 makes the two bars comprised in the locking mechanism 2a, 2b to slide in opposite directions. The apposed slanted faces of those bars slide against each other in a ratchet motion. When this happens, the invention locks, exerting the necessary force to maintain the needle still. Once the needle is tightened, the turning knob 5 is turned in order to create a rotational movement on the rod 10 where it is attached. The force exerted on that rod 10 also rotates the other rod 9. When the desired angle is attained, the surgeon will drive the needle through the tissue as the rods 9, 10 roll the needle out. When the desired rotation is completed, the surgeon releases the locking mechanism 2a, 2b by pulling towards him the pulling piece 6. This movement is made until the tooth of the locking bar attached to the pulling piece 6 passes the last tooth of the locking bar attached to the transverse plate 3. When this occurs, the locking bar attached to the pulling piece 6 is disengaged from the transverse plate 3 locking bar and the invention is finally unlocked. The bar attached to the pulling piece 6 will be forced down and forward loosening up the rods 9, 10. This method is repeated on the other tissue that wants to be joined to the tissue already perforated by the needle. All the above is repeated as many times as stitches have to be performed.

Figure 2A:
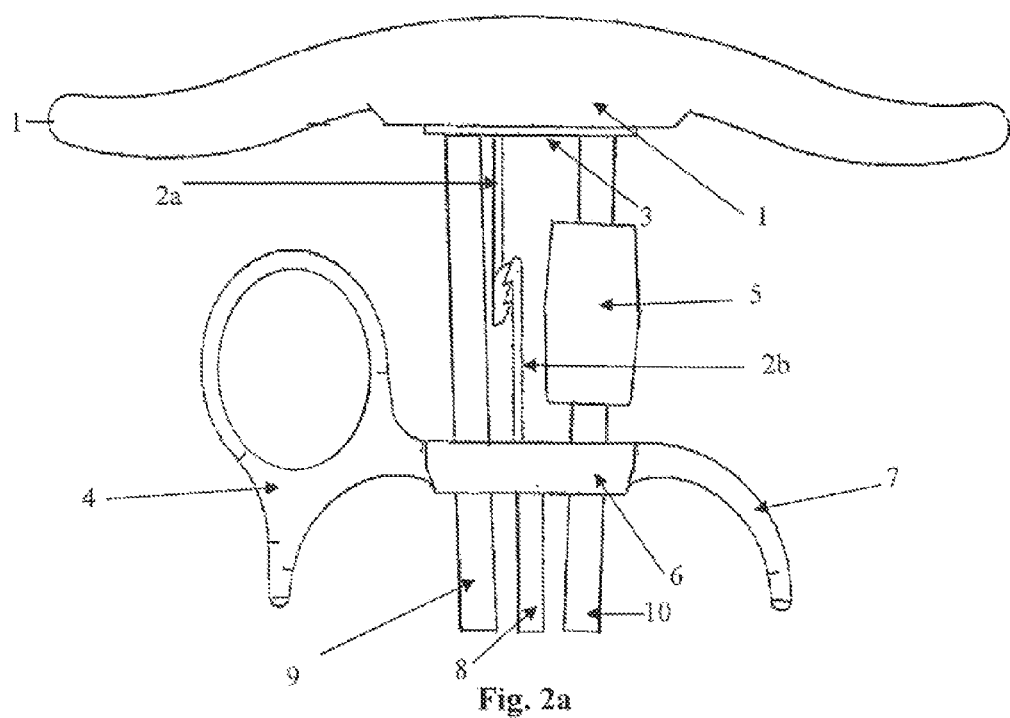
FIG. 2A shows the Pull-locking Rotational Action Needle Driver device unlocked.
Figure 2B:
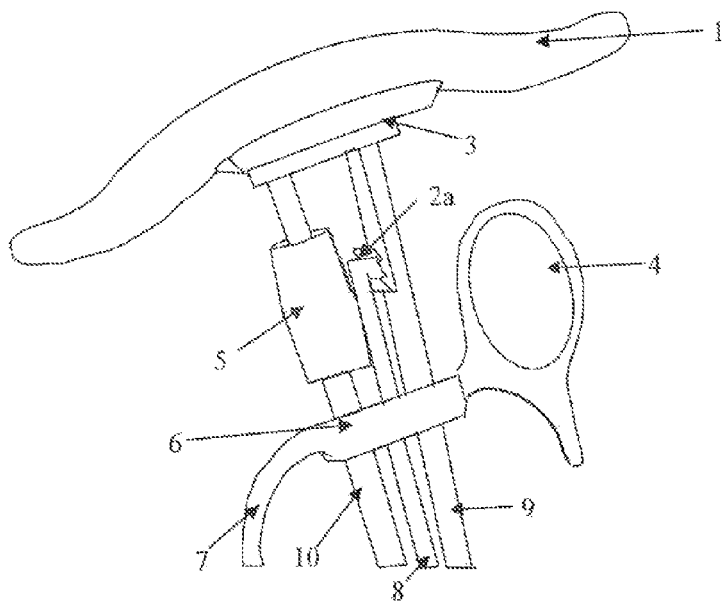
FIG. 2B shows the Pull-locking Rotational Action Needle Driver device lock over the first tooth over the triple-teeth component.
Figure 2C:
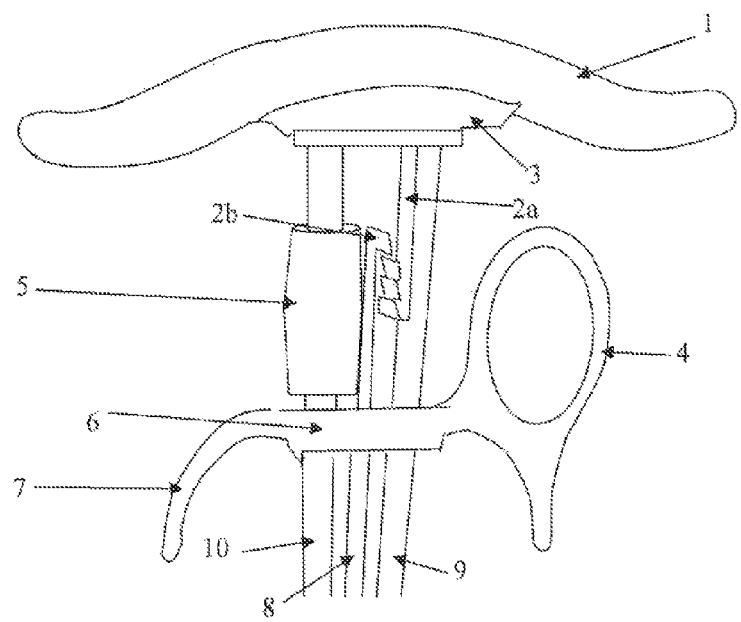
FIG. 2C shows the Pull-locking Rotational Action Needle Driver device lock over the last opposing tooth over the triple-teeth component.
Figure 2D:
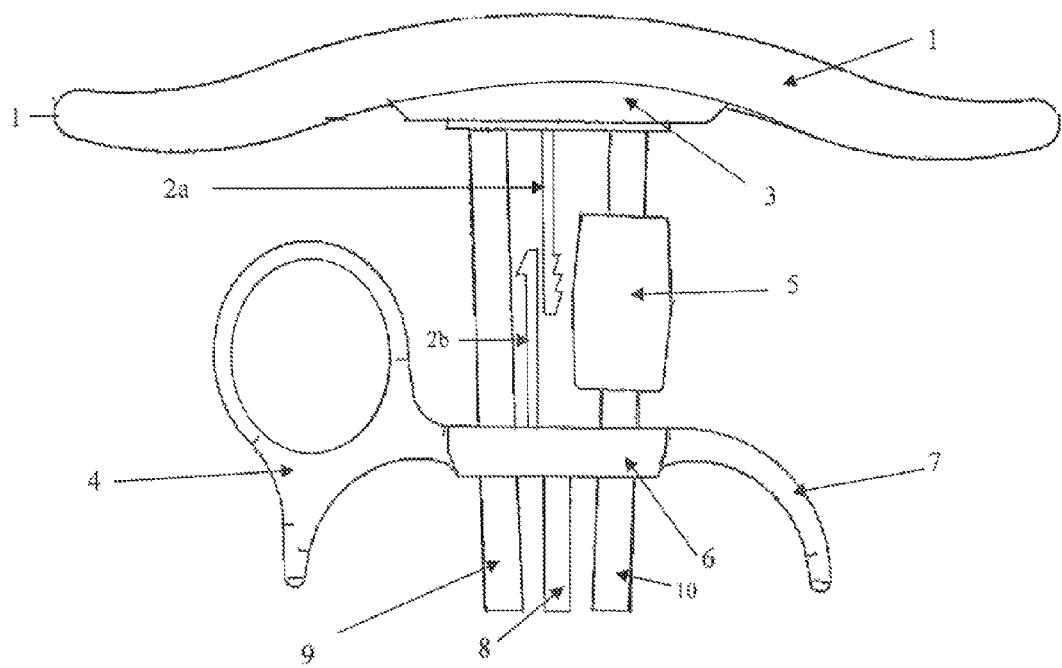
FIG. 2D shows the Pull-locking Rotational Action Needle Driver device unlock at the position of the sequential motion locking mechanism.

Particularly, the pull locking mechanism in first embodiment is illustrated in FIGS. 2A to 2D, wherein it is shown the stepwise motions of the said locking mechanism components relative to each other. In FIG. 2A, the components are shown with the slanted surfaces of the teeth facing each other. At this point the components are not yet engaged and the instrument is still unlocked. In FIG. 2B however, the pulling motion drives the single-toothed component 2b over the first tooth of the triple-teeth component 2a. The flat backsides are apposed and the instrument is locked. Please note the smooth curved underside of the single-toothed component 2b. This feature will become important once the locking mechanism is disengaged. The next step is described in FIG. 2C, wherein after further pulling is exerted, the single-toothed component 2b locks on subsequent opposing teeth. A final pull will drive the single tooth over the last opposing tooth. At this moment the locking mechanism is disengaged and the instrument is unlocked as shown in FIG. 2D. The recoil of the instrument will force the components apart. Please note the curved underside of the triple-teeth component 2a. The smooth curved outlines of both components will face each other. The single-tooth component 2b will travel forward to its initial position as it slides down and under the curved underside of the triple-teeth component 2a.

Figure 3A:
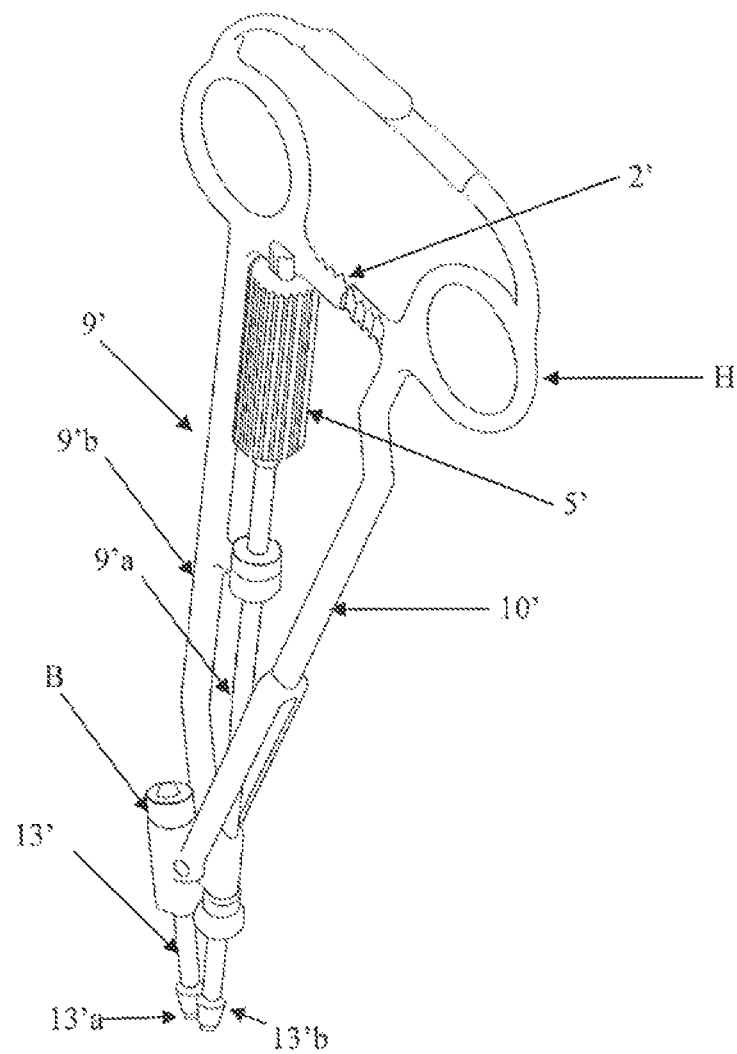
FIG. 3A shows an isometric view of a second embodiment of a rotational Action Needle Driver device.
Figure 3B:
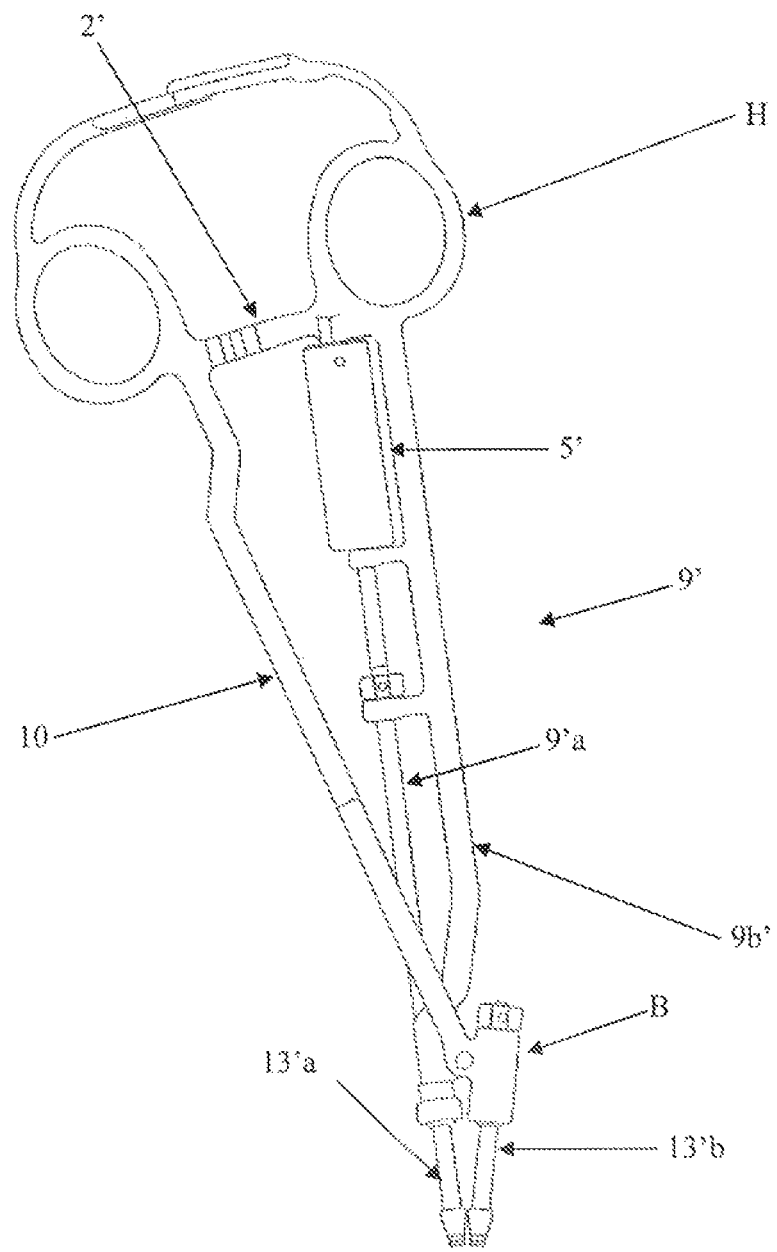
FIG. 3B shows a side view of a second embodiment of a rotational Action Needle Driver device.

FIG. 3a and FIG. 3b discloses a second embodiment employing a rotational driver 5', wherein said second embodiment comprises an interactive portion comprising a first extended member 9' and a second extended member 10' wherein said extended members contact each other at a distal end 13'. The second embodiment provides a locking mechanism 2' at the handle, wherein said handle is connected to the first extended member proximal end and the second extended proximal end. The rotational motion system comprises a rotational actuator 5' which mechanically connected to a transmission device 5'a. The transmission device comprises a rod connected to the first extended member distal end 13'a in order to provide the desired rotational motion. The rod 9a' is firmly supported by a supporting body 9'b. The main purpose of said supporting body 9'b is to hold in position the actuator, the rod and the first extended member distal end 13'. The first extended member and the second extended member are cross at a area substantially close to the distal end 13', cross area has securing means B for pivotally securing the cross members.

The second extended member, as mentioned before, is fixed to said handle at the second proximal end. The second distal end 13'b contacts the first distal end obliquely in order to concentrate the contacting force on the first contact distal end 13'a and the second contact distal end 13'b. The second extended member main body is divided in a first part 10'a and second part 10'b, wherein said two parts are mechanically connected by means of a bearing B which assists with the second 13'b distal end rotational movement.

Figure 4:
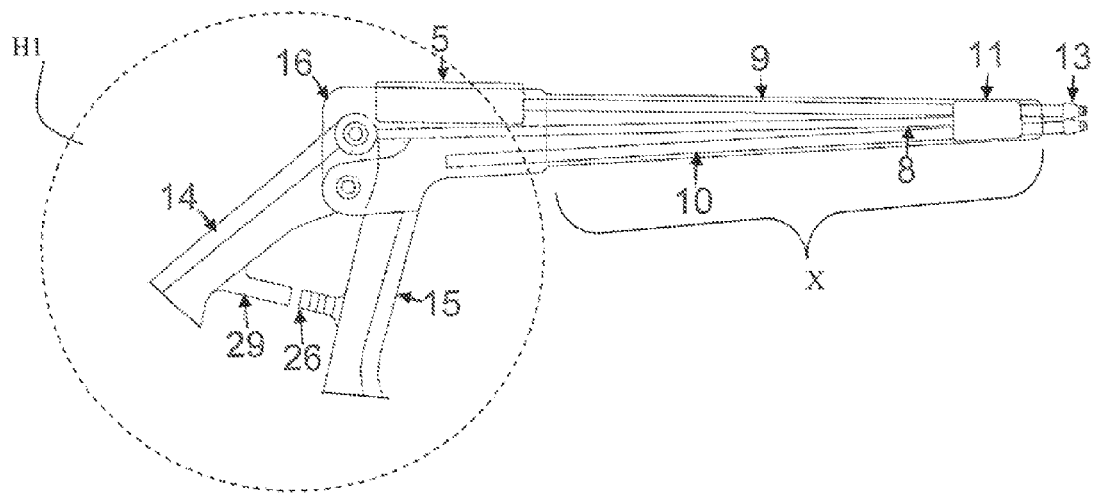
FIG. 4 shows a side view of a third embodiment of a rotational Action Needle Driver device used in a laparoscopic instrument with a first lineal motion mechanism.
Figure 5A:
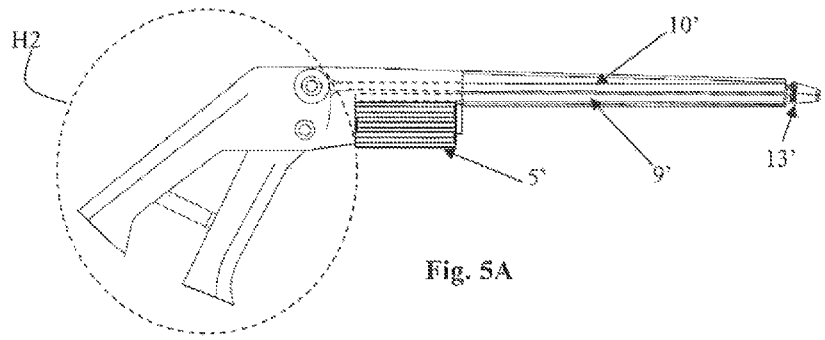
FIG. 5A-5D shows the Rotational Action Needle Driver used in a laparoscopic instrument with a second lineal motion mechanism.
Figure 5B:
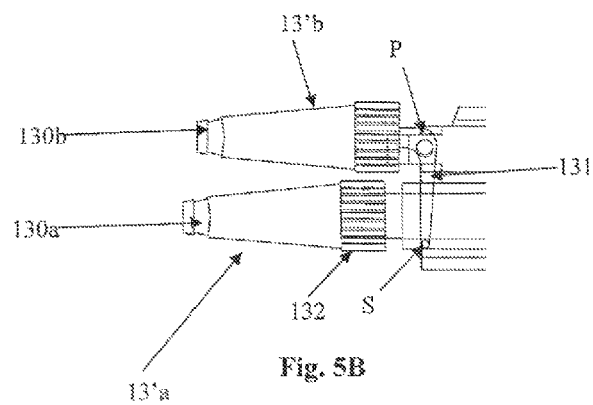
Figure 5C:
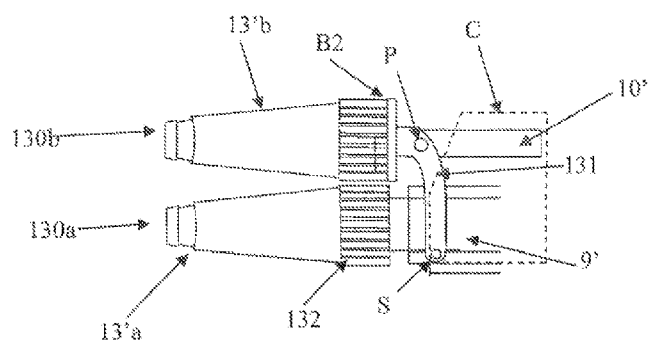
Figure 5D:
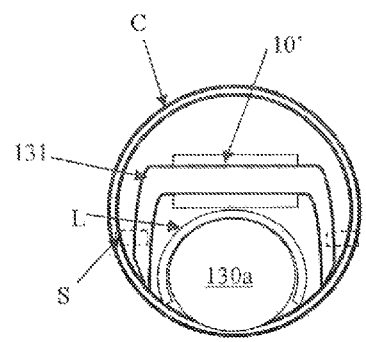
Figure 6A:
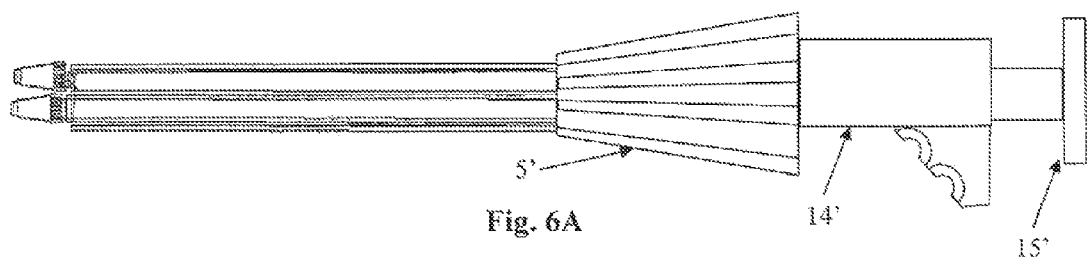
FIG. 6A-6D shows the Rotational Action Needle Driver used in a laparoscopic instrument with a second handle embodiment.
Figure 6B:
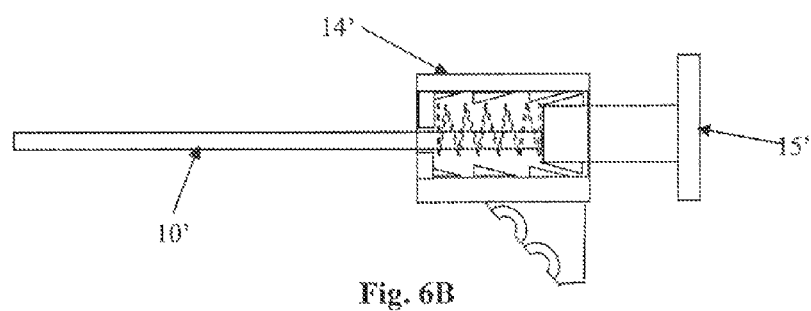
Figure 6C:
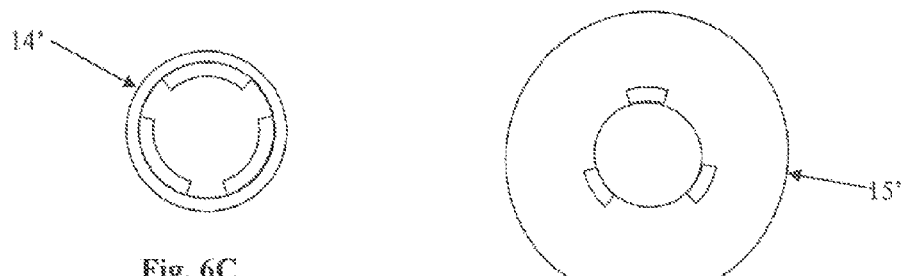
Figure 6D:
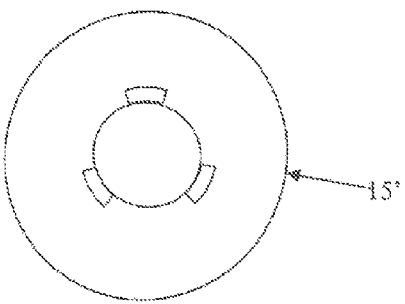

FIG. 4 discloses a third embodiment, wherein the rotational actuator is incorporated in a surgical instrument use in laparoscopic surgery, more particularly in the suturing process of laparoscopic surgery. The present invention comprises a set of rods 9,10, a rotational actuator 5 and a pulling mechanism substantially similar to the first embodiment. In this third embodiment the handle H1 is arranged to provide a pulling action performed by compressing a movable part 14 against a static element 15. The static element 15 comprises two sections diagonally attached. The movable element 14 is pivotally attached to a point close to the intersection between the sections of the static element 15. The overall shape of the elements will be designed for ergonomics and comfort. The handle H1 incorporates a locking system 29, 26 and a cover 16 that holds statically said static portion 15 and serves as pivot joint to said movable element 14. Further the extender members 9,10, more particularly the extender member main body X is longer to reach farther places, as is commonly know in laparoscopic instruments.

FIG. 5a-5d, discloses a fourth embodiment comprising a interactive portion comprising extended members 9',10' mechanically connected to the handle H2 which is similar to the handle provided for the third embodiment, wherein said handle comprises a movable element 14 and a static element 15. Also this embodiment is used in laparoscopic surgery, more particularly in the suturing process of laparoscopic surgery.

The forth embodiment rotational actuator 5' is located close to the handle's movable element 14 and a static element 15 for easy assess for the user after locking the locking mechanisms. Further de distal end 13' comprises a first distal end 13b' and a second distal end 13'a, wherein said second distal end contact the first distal end in a oblique manner in order to concentrates the compressing force in a particular point such as the first distal contact 130a and the second contact distal end 130b. The fourth embodiment comprises a linear motion system, wherein said linear system control the displacement of said second distal end 13'b toward the first distal end 13'a for performing a holding or compressing action at the first distal contact 130*a* and the second contact distal end 130*b*. The linear system employs said second extended member 10' to provide the linear motion by means of the movable element 14 at the handle, wherein a compressing action or pulling action toward the static element 15 in combination with the second extended element 10' generates the displacement at the second distal end 13'*b* and first distal end 13'*a*. The displacement at the second distal end 13'*b* toward first distal end 13'*a* is assisted by means of an oblique motion control mechanism. The oblique motion control mechanism comprises a main holding member 131, wherein said main holding member 131 connects with the second distal end 13'*b* at one extreme and the other extreme to a static portion C, in the instant case the casing, by mean of first pivot join S. The main holding member 131 is mechanically connected to the second extended body by a second pivot join P and fixed to said second distal end 13'*b*. It is positioned between said second extended member 10' and said second distal end 13'*b*.

The main holding member 131 assists and control the oblique contact of the first distal end 13'*b* and the second distal end 13'*a*. As mentioned before the second extended member 10' moves forward or backwards due to the movable element motion 14. The linear displacement of the second extended element 10' is transfer to said main holding member 131 as a oblique motion, wherein said oblique motion is control or limited by the first pivot join P and the second pivot join S. During the linear motion of the second extended member some friction is generated between the second extended member 10' and the first extended member 9'. A sheet or elongated sheet L is provided between the two members to reduce or avoid friction. The elongated sheet is meat to be thin in order to reduce the apparatus thickness at the distal end.

FIG. 6*a*-6*d* shows a second embodiment for the handle, however is important to understand that the present invention may be operated with any handle capable to provide or generate a linear motion for the second extended member while locking said member at a desired position. The second embodiment for the handle comprises a movable element 15' and a static element 14', wherein said static member comprises several protrusions that interacts with protrusions at the movable element 15' in order to hold the displacement of the second extended member 10' at a desired position. The locking action of said handle may be avoid by turning said movable element 15' in a manner that protrusion on the static element 14' do not contact the protrusions of the movable element 15'. Further a resilient member pushes the movable to the original position.

Figure 7A:
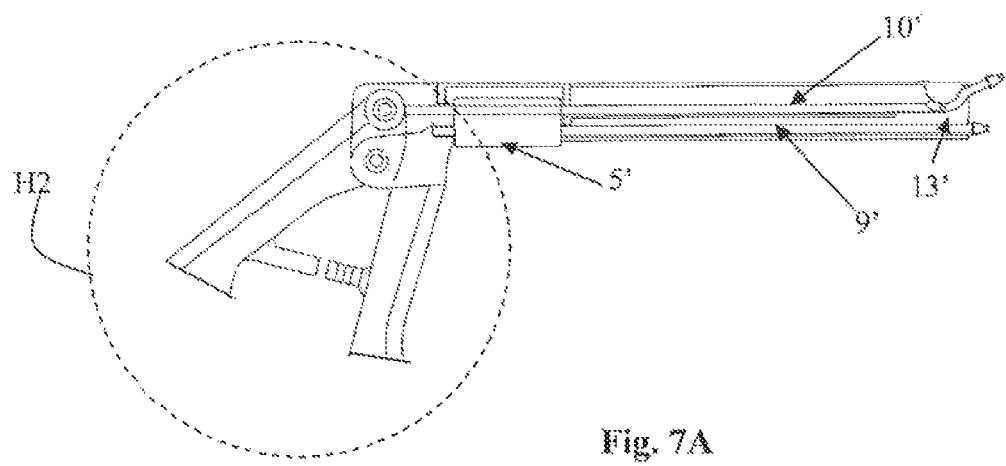
FIG. 7A-7B shows the Rotational Action Needle Driver used in a laparoscopic instrument with a third lineal motion mechanism.
Figure 7B:
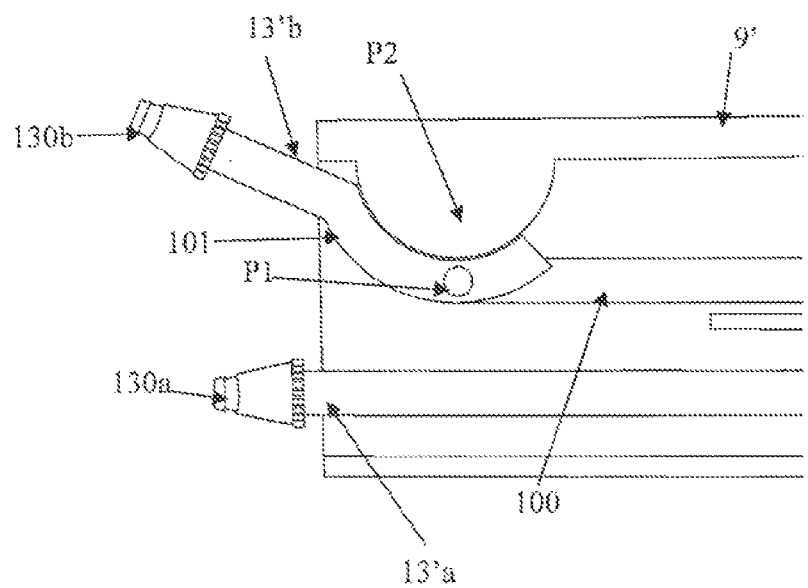

FIG. 7*a*-7*b* shows a fifth embodiment also directed, but no limited to laparoscopic surgery. The fifth embodiment comprises a handle H2, similar to the one mentioned before, and a rotational actuator close to said movable and static elements. The distal end 13' in the instant embodiment provides the oblique connection between the first distal end 13'*a* and the second distal end 13'*b*. However different form the oblique motion control system. The present oblique motion control system comprises a contour path P2 and a slide portion 101, wherein said slide portion 101 is connected to the second extended member 100 by a third pivot join P1, wherein said pivot join assists the oblique motion of the second distal end 13'*b* due to the slide portion 101 curved shape. In order words the linear movement provided by the second extended member 100 is transferred in an oblique movement at the second distal end 13'*b* by means of the displacement of a slide portion 101 over a contour path P2. As mentioned before the forward and backward movement of the second extended member 100 is proportional to the oblique motion displacement. It has to be understood, as mentioned before, that the oblique motion and contact of the distal ends 13'*b*, 13'*a* is meant to concentrate most of the compressing force between the first contact distal end 130*a* and the second contact distal end 130*b* or the a needle located between said contact ends for suturing purposes.

Figure 8A:
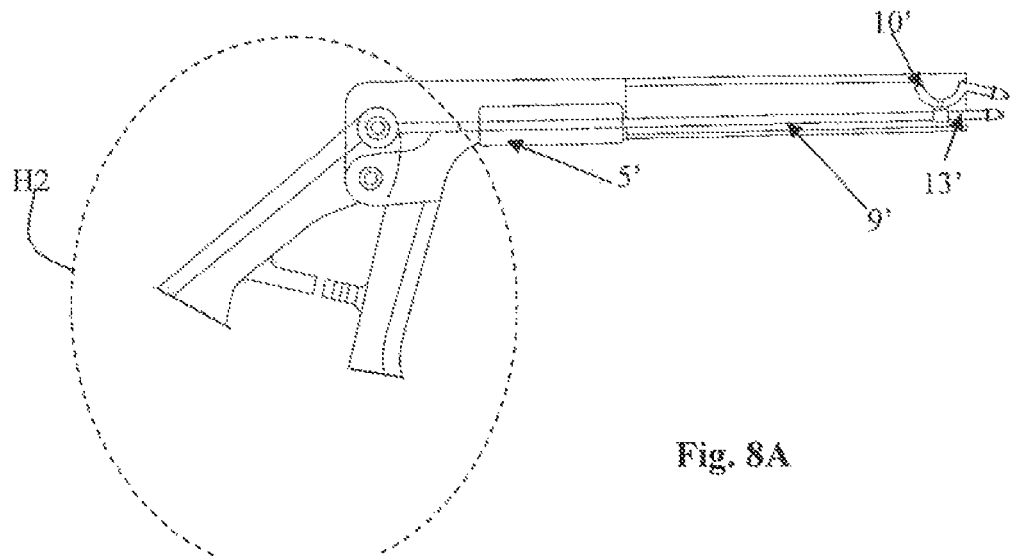
FIG. 8A-8B shows the Rotational Action Needle Driver used in a laparoscopic instrument with a fourth lineal motion mechanism.
Figure 8B:
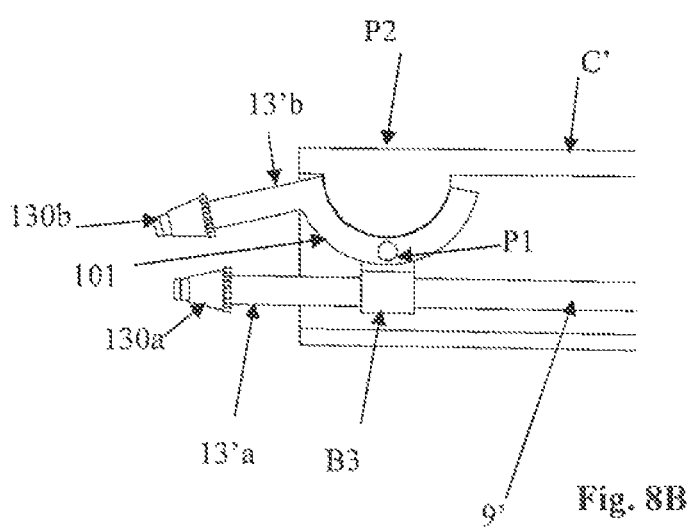

FIG. 8A-8B discloses a sixth embodiment which is closely similar to the fifth embodiment, wherein the main difference is the use of a distal end 13', more particularly the oblique motion control system. In the instance case the oblique motion control system comprises a contour path P2, which is part of the casing inner wall, and a slide portion 101, wherein said slide portion 101 instead of being connected to a second extended member is connected to the first extended member 9', wherein said first extended member 9' provides linear motion which is transmitted to said slide portion by mean of a fourth pivot join P1. The linear motion for said first extended member 9' is generated at the handle, as explained before, wherein said first is connected to the movable element and the static element is just fix to the handle. The slide portion 101 is connected to a bearing that only allows rotational motion of the first extended. member 9' inside said bearing B3. The forward and backward movement of the first extended member 9' is converted into oblique motion, wherein the oblique motion, as explained before in controlled by means of said contour path P2 and said slide portion 101 shape.

Figure 9A:
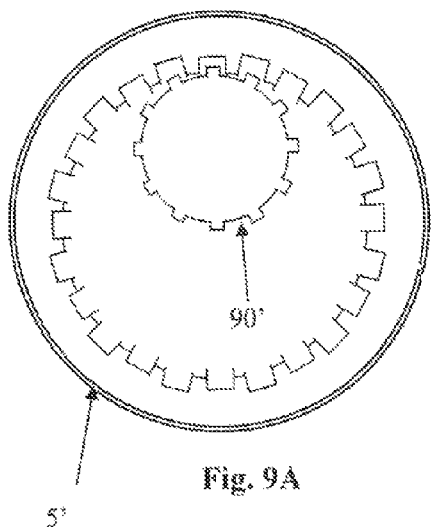
FIG. 9A-9C shows the rotational actuator mechanical connection with rotational rod.
Figure 9C:
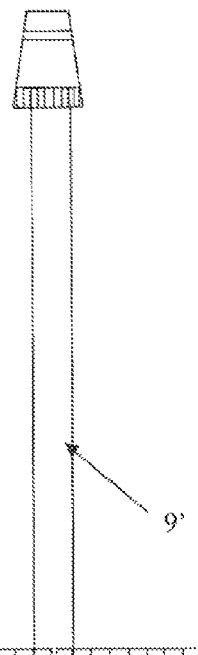
Figure 9C:
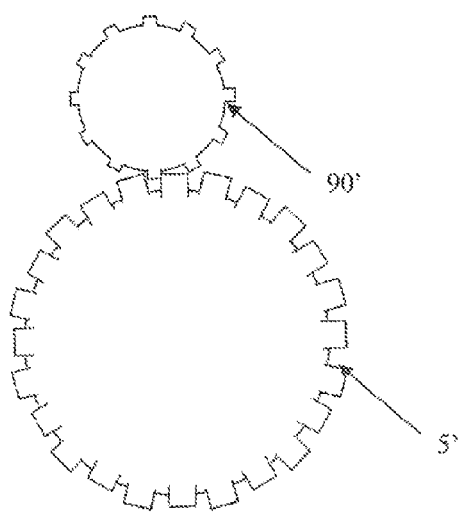
Figure 9B:
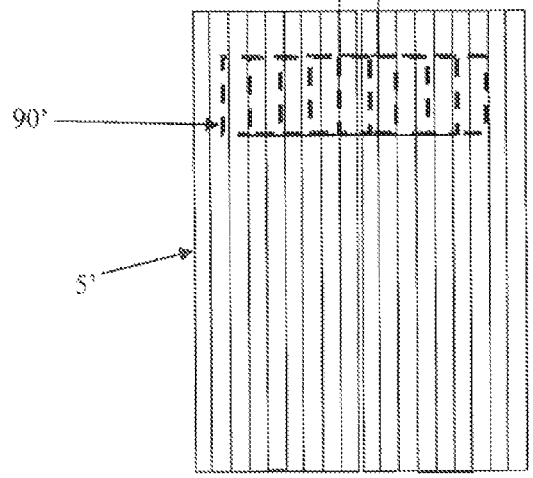

FIGS. 9A-9C are directed to the mechanical connection between the rotational actuator 5' and the first extended member 9'. As mentioned before, the rotational actuator 5' initiates and transfers the desired rotational action from the user to the first distal end 13'. Several mechanical connections can be employed, however it has to be understood that the mechanical connection affects directly the rotation of the needle during the suturing process. In the instant case two basic connections are provide. For example FIG. 9A-9B shows a first extended member proximal end comprising a transmission device, such as a gear 90' connected to said proximal end in order to transfer the rotational motion at the actuator 5' toward said first distal end 13'*a*, wherein said gear is located inside of the actuator 5' contacting the inner surface. FIG. 9*b* discloses a first extended member proximal end comprising a transmission device, such as a gear 90' connected to said proximal end, wherein said gear is located outside of the actuator 5' contacting the outer surface. This two connections have different results on the distal end movement and therefore on the needle. FIG. 9C provides a needle motion in the same direction of the actuator 5'.

FIG. 10A-10D The driven rod 20 and slave rods 21 are obliquely positioned coming into contact at their respective distal ends having fluted surface creating a needle-grasping portion or contact distal end 28, around each rod surface for better positioning of the needle 11.

Further the FIG. 10*a*-10*d* is directed to the distal end movement and contacting action. As mentioned before, the first distal end 13*a'* and said second distal end 13'*b* contact each other in an oblique manner that concentrates the force on a particular point or area, wherein said area is the needle-grasping portion distal or contact area 130*a*, 130*b* where the needle is located to be driven. It is important to understand that the use of obliquely positioned rods provide a better control of the portion to be press contrary to parallel rods, wherein the area where the force is applied is bigger and therefore the contacting point of force is transmitted or distributed over the whole contacting surface. The distal ends are made of any selected material capable to perform at least the functions herein mentioned. The selection of the material depends on the field the device is going to be employed. Also the contact distal end is preferred to have a surface that assist the performed action. For example, while using the device in a suturing process is preferred to have a distal end or contact distal end surface cover with a material, such as but not limited to rubber, that provide some friction over the needle in order to keep a constant displacement of said needle.

Figure 10A:
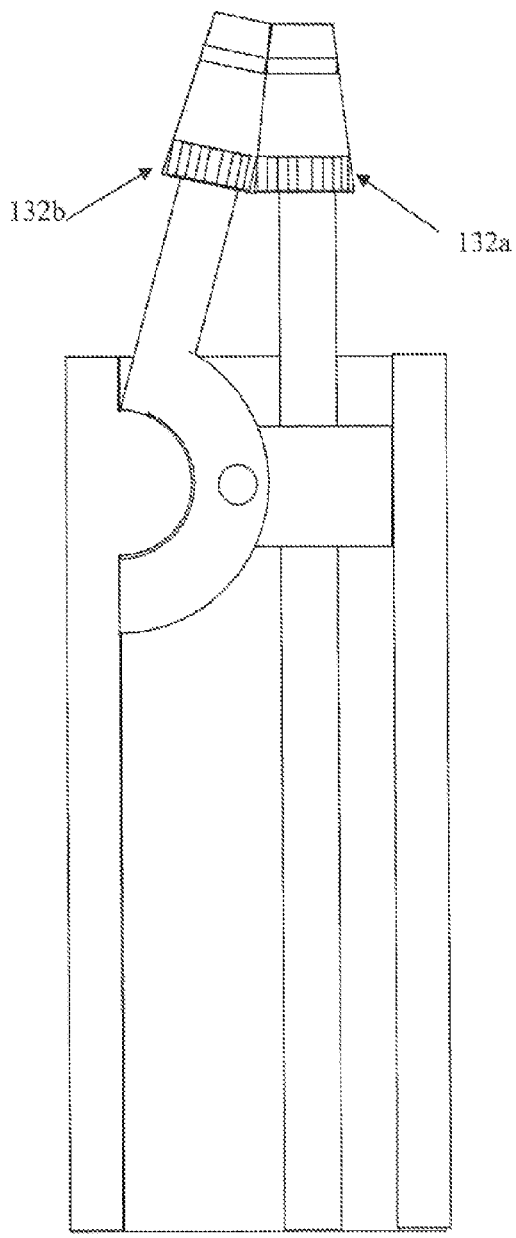
FIG. 10A-10D shows distal end rotational transmission device
Figure 10B:
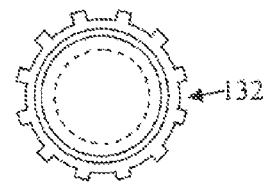
Figure 10C:
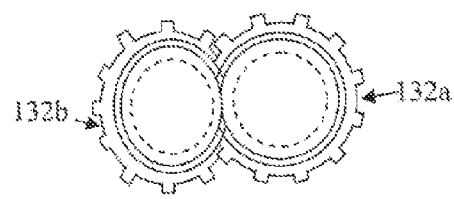
Figure 10D:
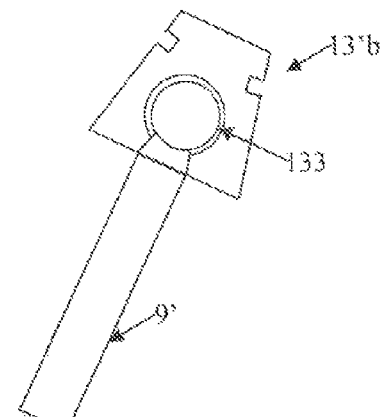

Further the transmission mechanism or gear 132 regulates the rotational movement between the first distal end and second distal end as shown in FIG. 10C. The second distal end comprises a bearing mechanism, such as a ball bearing 133 that assist with the rotation of said distal end when the first distal end contacts said second distal end. Additionally using a device with detachable and/or disposable distal ends or interactive portions offers several benefits to the user and the device. For example, if the users need to change the distal end due to changes in needle size a simple change of distal end and/or interactive portion would be enough to continue performing the suturing process without the need of an extra device.

Figure 11A:
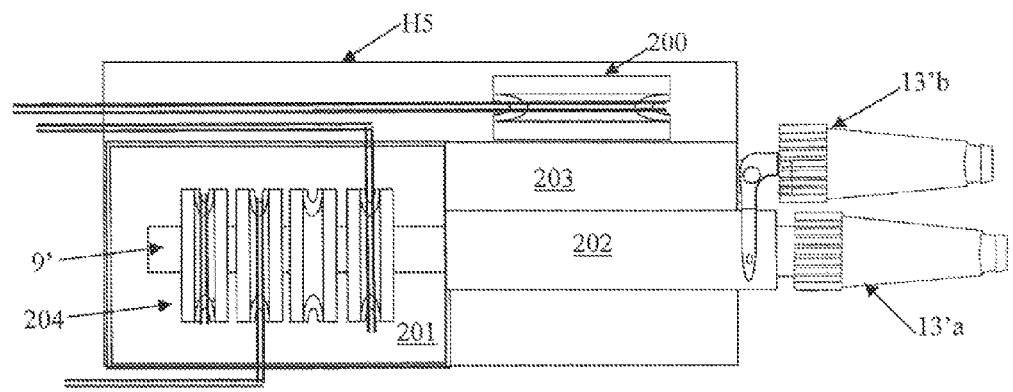
FIG. 11A-11F shows the Rotational Driver device drive by pulleys mechanisms.
Figure 11B:
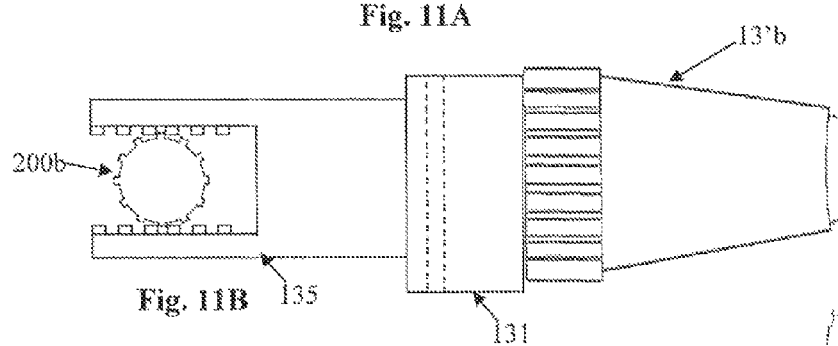
Figure 11C:
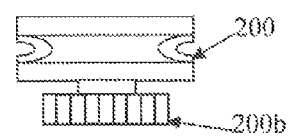
Figure 11D:
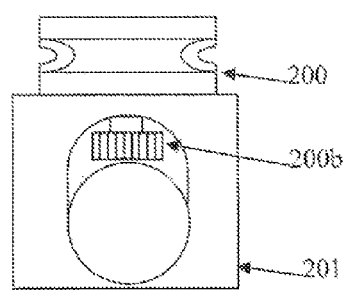
Figure 11E:
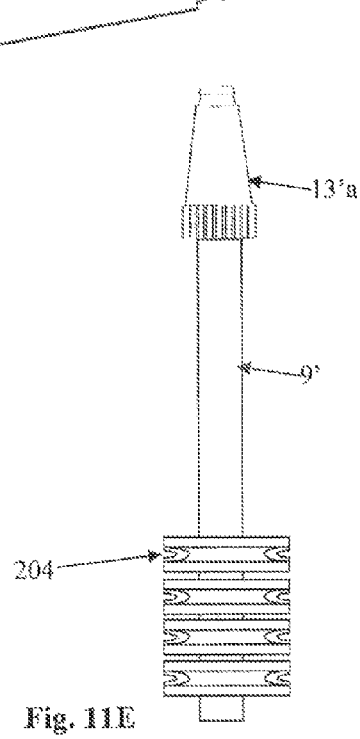

FIG. 11A-11F is directed to the use of pulley and wires to provide the desired motion herein mentioned. For example, as shown in FIG. 11A a system of pulley is connected to a case 203, wherein said casing enclose the linear motion system for said second extended member. Closely similar to the oblique motion control mechanism, as mentioned before for FIGS. 5B-5D comprises a main holding member 131 connects with the second distal end 13'b at one extreme and the other extreme to a static portion 202, in the instant case the casing of the first extended member 9', by mean of first pivot join S. The linear motion is controlled by a transmission device 200b coupled to a pulley 200, wherein the rotational movement of the pulley 200 is transferred to said gear 200b and convert to a linear motion by means of a teeth structure 135.

Figure 11F:
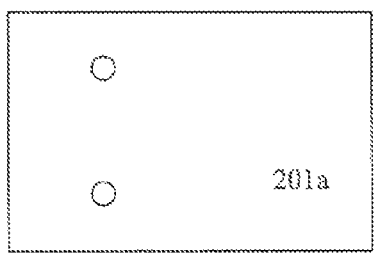
Figure 11F:
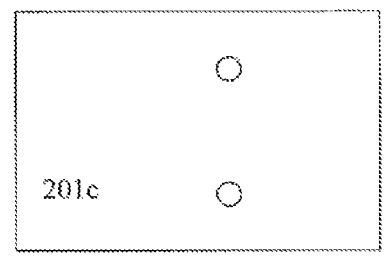
Figure 11F:
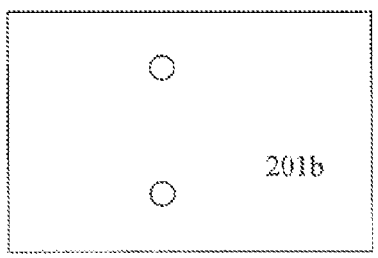
Figure 11F:
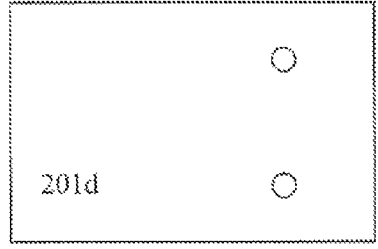

Further the rotational motion of the first extended member 9' is accomplished by providing a rod connected to a first distal end at one extreme and to at least a rod pulley 204. Two casings are covering said first extended member. The first casing 201 is covering the pulley or pulleys 204 at the end and the second casing 202 is covering part of the rod of the first extended member 9' and serving as support for the linear system casing 203. The first casing comprises several channels that permit the wires to interact with said pulley 204. In the instant case more than one pulley 204 is connected to said rod, therefore several channel are need. The first casing 201 is provided with shifted channel at different positions, as shown in FIG. 11F. The main purpose of the arrangement of channels is to provide a rod that even when a wire interacting with a pulley is not tight enough other pulley can provide the rotational action over the distal end 13'a.

The invention as describe above provide several benefits, some of the benefit are:

A) Rotational Action:

The use of rods that rotate while grasping the needle enables this instrument to perform tasks that other drivers cannot perform. The most important of these features is the ability to drive the needle continuously through the tissue without the need to release and re-drive the needle. Once the needle has been rotated to a favorable position it can be grasped at the other side of the free tissue edge. The needle can even be repositioned again, if desired, by rolling the graspers or the surgeon may proceed directly to the other tissue edge. Thus, there is no need to release, re-grasp, and re-drive the needle. The process is repeated in the same manner and a suturing cycle is completed. Automatically, this eliminates six steps out of the fourteen needed per cycle. In addition, this feature decreases the amount of time, effort and eye-hand coordination that the surgeon invests in performing these tasks. This is especially true when small needles need to be used. In this scenario the surgeon will likely have to pick up the needle and reposition it manually for each tissue purchase that he takes. This is done so because the size of the needle may make driving and re-driving the needle with a conventional driver impractical in terms of time and effort.

As explained earlier, handling of the needle portends a very serious occupational risk for the surgeon. If this instrument can reduce or eliminate this risk, then a very significant benefit can be derived from using this needle driver beyond time-efficiency. In addition the instrument's design allows a reduction or elimination, if desired, of the rotational motion required at the surgeon's wrist to drive the needle through the tissue. This affords the surgeon the capability of driving the needle with minimal motion of the hand. In deep tissues this translates to more efficient and precise handling of the needle. Such a capability is especially important when vascular structures are in the vicinity of the area to be sutured. Reducing wrist rotation may also reduce any potential interference with the line of sight when the operative spaces are very small or narrow, as in the brain.

B) Locking Mechanism:

As shown earlier, this design incorporates a pull-locking mechanism that makes the instrument more versatile than commonly used needle drivers. The instrument can be locked and unlocked with the same unidirectional motion. As a result, the surgeon does not have to move his hand or fingers any differently when locking or unlocking the instrument. This feature reduces the amount of movements and energy expenditure. Thus, the surgeon's hand experiences less fatigue.

Another advantage inherent to the instrument's locking mechanism is that it eliminates handedness. Common needle drivers are designed to unlock easily when handled by right-handed surgeons. There are also needle drivers designed for left-handed surgeons. However, for an institution this implies doubling the cost of instrumentation for no reason other than handedness. By placing the locking mechanism in a neutral position this problem is eliminated. The instrument is locked and then unlocked by pulling on the tabs towards the handle. This movement will proceed in the same direction no matter which hand is used. Therefore, the left-handed surgeon will not have to spend any excessive time or effort learning how to compensate for a needle driver's design. Left-handed surgeons will also avoid the extra energy expenditure that comes with unlocking a right-handed instrument.

C) Finger Positioning (if Required by Instrument):

This instrument is designed so that most fingers can be positioned similarly to how they would be poisoned in a commonly used needle driver. This feature makes handling this instrument a more familiar experience for the surgeon. Although the instrument is different from the usual needle drivers it is not designed to feel alien to the surgeon's hand. Thus, this instrument empowers the surgeon with new capabilities while retaining a hand position to which he or she is already accustomed.

D) Multiple Ways to Drive a Needle:

As previously explained this instrument is able to grasp the needle in multiple ways. The usual needle placement allows needle movement in a plane perpendicular to the instrument's long axis. However, in very deep, conical spaces this arrangement implies a lot of maneuvering in an attempt to purchase the desired tissue. Adjacent structures may interfere with the instrument or with needle movement.

This needle driver design provides for grasping the needle so its curvature lies in plane with the long axis of the instrument. The needle can be positioned so it needs much less area for maneuvering.

E) Multiple Ways to Hold and Operate the Instrument:

This design permits rotation of a curved surgical needle without requiring a rotational motion of the wrist. Therefore, the instrument can be held in a position that may not allow wrist rotation and still carry out its function. In some situations the structures to be sutured lie very deep. Doing surgery on the vertebral column of very obese patients is one such situation. For example, if the dura mater (a membrane that protects and envelops the spinal cord) is cut it needs to be sutured. The dura mater lies within a deep constricted space. In a very obese patient the additional thickness of the adipose (fatty) tissue makes the dura lie even deeper from the surface. The surgeon may have to lean towards the patient and rotate the arm bearing the needle driver. This is necessary to get his forearm in a vertical position so he can maneuver the instrument properly. The new needle driver design may be operated while held like a t-shaped control lever. In this position the long axis of the instrument lies perpendicular to the palm of the hand. The surgeon does not need to position his forearm vertically in order to rotate the instrument. There is a powerful advantage when using this instrument that goes beyond any individual benefit granted by its design features. The fact that suturing can become a more streamlined process permits a more continuous flow of the procedure. The surgeon does not have to stop as often to think what he needs to do next, He does not need to refocus on which segment of the tissue to grasp after looking away from the tissue to reposition a needle. The end result is a procedure that is faster, more energy-efficient and safer for both the patient and the surgeon.

The invention is not limited to the precise configuration described above. While the invention has been described as having a preferred design, it is understood that many changes, modifications, variations and other uses and applications of the subject invention will, however, become apparent to those skilled in the art without materially departing from the novel teachings and advantages of this invention after considering this specification together with the accompanying drawings. Accordingly, all such changes, modifications, variations and other uses and applications which do not depart from the spirit and scope of the invention are deemed to be covered by this invention as defined in the following claims and their legal equivalents. In the claims, means-plus-function clauses, if any, are intended to cover the structures described herein as performing the recited function and not only structural equivalents but also equivalent structures.

All of the patents, patent applications, and publications recited herein, and in the Declaration attached hereto, if any, are hereby incorporated by reference as if set forth in their entirety herein. All, or substantially all, the components disclosed in such patents may be used in the embodiments of the present invention, as well as equivalents thereof. The details in the patents, patent applications, and publications incorporated by reference herein may be considered to be incorporable at applicant's option, into the claims during prosecution as further limitations in the claims to patentable distinguish any amended claims from any applied prior art.

What is claimed is:

1. A rotational driver comprising:
   interactive portions comprising a first extended member and a second extended member;
   a rotational system;
   a linear motion system;
   wherein said first extended member comprises a detachable first distal end, a first proximal end and a first main extended member body, wherein said first main extended member body is between said detachable first distal end and said first proximal end, wherein said detachable first distal end comprises a first contact distal end;
   wherein said second extended member comprises a detachable second distal end, a second proximal end and a second main member body, wherein said second main member body is between said detachable second distal end and said second proximal end, wherein said detachable second distal end comprises a second contact distal end;
   wherein said rotational system comprises a rotational actuator mechanically coupled to at least an action transmitter mechanism, wherein said action transmitter mechanism is mechanically connected to said first extended member providing rotating action upon said detachable first distal end;
   wherein said detachable first distal end and said detachable second distal end contact each other in a continuous oblique manner by means of said linear motion system, wherein said linear motion system comprises mechanical means to provide displacement of said detachable second distal end with respect to said detachable first distal end and wherein said detachable second distal end displacement exerts compressing force at said detachable first distal end, wherein said compressing force is concentrated at said first contact distal end and said second contact distal end by means of said continuous oblique contact; and wherein the rotating action upon said detachable first distal end transmits a second rotation action in the opposite direction upon said detachable second distal end retaining the continuous oblique contact for 360 degrees.

2. The rotational driver of claim 1 wherein said detachable second distal end comprises a bearing that assists with a rotational motion of said detachable second distal end.

3. The rotational driver of claim 2 wherein said detachable second distal end comprises a second transmission device and said detachable first distal end comprises a first transmission device that assists to transfer the rotational motion of said detachable first distal end to said detachable second distal end.

4. The rotational driver of claim 1 wherein said second contact distal end comprises a second distal end annular groove, and wherein said first contact distal end comprises a first distal end annular groove.

5. The rotational driver of claim 1 wherein said linear motion system comprises mechanical means to provide angular displacement between said detachable first distal end and said detachable second distal end.

6. The rotational driver of claim 1 further comprising a locking mechanism, wherein said locking mechanism fixes the linear motion system in a particular position.

7. The rotational driver of claim 6 further comprising a handle, wherein said handle comprises a part that is operated by hand and is positioned away from the detachable first distal end and substantially closer to the first proximal end and is mechanically coupled to at least one of said first extended member and said second extended member and wherein said locking mechanism is substantially located at the handle.

8. The rotational driver of claim 7 wherein said interactive portions, said rotational system, said linear motion system, said locking mechanism and said handle are combined in a suturing surgical instruments applied in surgical procedures.

9. The rotational driver of claim 8 wherein said surgical procedures comprises laparoscopic surgery and robotic surgery.

10. The rotational driver of claim 7 wherein said linear motion system comprises
- a static structure, wherein said static structure comprises a housing for said first main extended member body and said second main member body,
- a pulling arm, wherein said pulling arm provides a linear displacement with respect to said static structure of an extended member, wherein said extended member is selected from said first extended member and said second extended member,
- a contour path, wherein said contour path is physically connected to the static structure and assists the detachable second distal end displacement,
- a pivoting portion, wherein said pivoting portion pivots said detachable second distal end and assists the detachable second distal end displacement, and wherein said locking mechanism is mechanically coupled to the pulling arm to fix said pulling arm at a pre-determinate displacement.

11. The rotational driver of claim 1, wherein said rotational system comprises a third extended member comprising a main body coupled with at least a pulley, wherein said pulley is rotated by transmission means.

12. The rotational driver of claim 11, wherein said transmission means comprises cables or wires.

13. A rotational driver comprising:
- interactive portions comprising a first extended member and a second extended member;
- a rotational system;
- a linear motion system;
- wherein said first extended member comprises a first distal end, a first proximal end and a first main extended member body, wherein said first main extended member body is between said first distal end and said first proximal end, wherein said first distal end comprises a first contact distal end;
- wherein said second extended member comprises a second distal end, a second proximal end and a second main member body, wherein said second main member body is between said second distal end and said second proximal end, wherein said second distal end comprises a second contact distal end;
- wherein said rotational system comprises a rotational actuator mechanically coupled to at least an action transmitter mechanism, wherein said action transmitter mechanism is mechanically connected to said first extended member providing rotating action upon said first distal end;
- wherein said first distal end and said second distal end contact each other in an oblique manner by means of said linear motion system, wherein said linear motion system comprises mechanical means to provide displacement of said second distal end with respect to said first distal end and wherein said second distal end displacement exerts compressing force at said first distal end, wherein said compressing force is concentrated at said first contact distal end and said second contact distal end by means of said oblique contact;
- a locking mechanism, wherein said locking mechanism fixes the linear motion system in a particular position;
- a handle, wherein said handle comprises a part that is operated by hand and is positioned away from the first distal end and substantially closer to the first proximal end and is mechanically coupled to at least one of said first extended member and said second extended member and wherein said locking mechanism is substantially located at the handle; and wherein said linear motion system comprises a static structure, wherein said static structure comprises a housing for said first main extended member body and said second main member body, a pulling arm, wherein said pulling arm provides a linear displacement with respect to said static structure of an extended member, wherein said extended member is selected from said first extended member and said second extended member, a contour path, wherein said contour path is physically connected to the static structure and assists the second distal end displacement, a pivoting portion, wherein said pivoting portion pivots said second distal end and assists the second distal end displacement, and wherein said locking mechanism is mechanically coupled to the pulling arm to fix said pulling arm at a pre-determinate displacement.

* * * * *